US008465521B2

(12) United States Patent
Cook et al.

(10) Patent No.: US 8,465,521 B2
(45) Date of Patent: Jun. 18, 2013

(54) METHOD AND SUTURE NEEDLE CONSTRUCT FOR CRUCIATE LIGAMENT REPAIR

(75) Inventors: James L. Cook, Columbia, MO (US); David O. Shepard, Naples, FL (US); Matthew C. Summitt, Naples, FL (US)

(73) Assignee: Arthrex, Inc., Naples, FL (US)

( * ) Notice: Subject to any disclaimer, the term of this patent is extended or adjusted under 35 U.S.C. 154(b) by 1800 days.

(21) Appl. No.: 11/546,391

(22) Filed: Oct. 12, 2006

(65) Prior Publication Data
US 2007/0135839 A1    Jun. 14, 2007

Related U.S. Application Data

(60) Provisional application No. 60/750,062, filed on Dec. 14, 2005.

(51) Int. Cl.
*A61B 17/04* (2006.01)
*A61B 17/06* (2006.01)

(52) U.S. Cl.
USPC .......................................... 606/228; 606/223

(58) Field of Classification Search
USPC ................. 606/138–139, 151, 144–146, 148, 606/222–229, 231–233, 300; 623/13.11–13.12, 623/13.14, 13.19, 13.2
See application file for complete search history.

(56) References Cited

U.S. PATENT DOCUMENTS

| | | | |
|---|---|---|---|
| 4,034,763 A * | 7/1977 | Frazier | 606/226 |
| 4,549,545 A * | 10/1985 | Levy | 606/228 |
| 5,545,171 A | 8/1996 | Sharkey et al. | |
| 5,645,568 A * | 7/1997 | Chervitz et al. | 606/228 |
| 5,683,415 A | 11/1997 | Brunken | |
| 5,984,933 A * | 11/1999 | Yoon | 606/148 |
| 6,533,802 B2 * | 3/2003 | Bojarski et al. | 606/232 |
| 6,547,807 B2 * | 4/2003 | Chan et al. | 606/228 |
| 6,716,234 B2 * | 4/2004 | Grafton et al. | 606/228 |
| 6,764,513 B1 * | 7/2004 | Dowling | 623/13.14 |

(Continued)

FOREIGN PATENT DOCUMENTS

| | | |
|---|---|---|
| FR | 2 867 380 | 9/2005 |
| FR | 2867380 A1 * | 9/2005 |
| WO | WO 01/56478 | 8/2001 |

OTHER PUBLICATIONS

Correspondence and records from Securos, Inc. regarding alleged knowledge, use and offer for sale of "Straight/Curved Swedged on Needles (Specialty Needles)," 2005 Product Catalog (alleged distribution in summer 2004).

*Primary Examiner* — Nicholas Woodall
*Assistant Examiner* — Larry E Waggle, Jr.
(74) *Attorney, Agent, or Firm* — Dickstein Shapiro LLP

(57) ABSTRACT

A suture needle construct and method for extracapsular ligament reconstruction in mammals. The joint is first is first explored, and the damaged ligament and meniscus are debrided. The joint capsule is closed and a tunnel is created at the appropriate location in the proximal tibia for tibial fixation. Subsequent to the formation of the tibial tunnel, a suture having a substantially curved needle at one end and a substantially straight needle at the other end is brought in the proximity of the joint. The suture is passed around the lateral fabella using the substantially curved needle, then deep to the patellar ligament using the substantially straight needle, and through the tibial tunnel using the straight needle. The needles are cut off, and the sutures are tensioned over repair site.

15 Claims, 5 Drawing Sheets

U.S. PATENT DOCUMENTS

| | | |
|---|---|---|
| 2002/0120280 A1* | 8/2002 | Wotton, III .................. 606/148 |
| 2004/0078046 A1 | 4/2004 | Barzell et al. |
| 2006/0052795 A1* | 3/2006 | White ......................... 606/102 |
| 2009/0216252 A1* | 8/2009 | Melvin et al. ................ 606/151 |

* cited by examiner

METHOD AND SUTURE NEEDLE CONSTRUCT FOR CRUCIATE LIGAMENT REPAIR

CROSS-REFERENCE TO RELATED APPLICATIONS

This application claims the benefit of U.S. Provisional Application Ser. No. 60/750,062, filed Dec. 14, 2005, the entire disclosure of which is incorporated by reference herein.

BACKGROUND OF THE INVENTION

The present invention relates to a method and suture needle construct for ligament repair and, more specifically, to a method and suture needle construct for extracapsular ligament reconstruction of mammals, in particular, canines.

DESCRIPTION OF THE RELATED ART

Various improvements in repairing damage to knee joints in human and non-human animals have been made over the years, some of the major advances involving endoscopic techniques and arthroscopic procedures. Arthroscopic surgery is particularly useful in excising or repairing damaged knee cartilage. Endoscopic techniques have been developed for use in repair and reconstruction of damaged anterior cruciate ligaments (ACL) and posterior cruciate ligaments (PCL).

Cruciate ligament repairs, particularly canine Cranial Cruciate Ligament (CrCL) repairs, are becoming increasingly important. The CrCL attaches to the femur, runs across the stifle joint, and attaches to the tibia. The CrCL holds the tibia in place and prevents internal rotation and hyperextension. CrCL rupture occurs primarily in the knees of dogs and cats, and it is one of the most common orthopedic injuries in dogs. CrCL rupture is also the most common cause of degenerative joint disease in the stifle joint. When a CrCL is torn, it causes sudden pain, instability in the knee joint, and often results in the pet holding its leg up. The pet may put the leg down and start using it within few days, but will continue to limp for several weeks. Typically, at the end of several weeks, the initial pain subsides and the pet will try to use its leg more; however, the joint remains unstable. Every time the animal puts weight on the leg, the tibia slides forward relative to the femur. This abnormal motion causes wear and tear on the joint cartilage, causing pain and leading to arthritis. This motion can also impart excessive stress on the menisci (C-shaped cartilage within the knee joint), causing damage or tearing.

Surgery is the only corrective measure for CrCL injuries. In the United States alone, the number of canine surgeries per year is estimated to be between about 50,000 to about 100,000, with the most common surgical CrCL repairs being tibial plateau leveling osteotomy (TPLO) and extracapsular repairs. The extracapsular repairs employ suture and represent about 70% of the total repairs. Surgery stabilizes the knee, allowing it to regain normal motion and therefore reducing the formation of arthritis.

An improved CrCL reconstruction technique is needed which provides increased fixation strength and optimal tension of the repair.

SUMMARY OF THE INVENTION

The present invention provides a method and suture needle construct for extracapsular ligament reconstruction in mammals. The joint is first explored, and the damaged ligament and meniscus are debrided. The joint capsule is closed and a tunnel is created at the appropriate location in the proximal tibia for tibial fixation. A suture having a substantially curved needle at one end and a substantially straight needle at the other end is brought in the proximity of the joint. The suture is passed around the lateral fabella using the substantially curved needle, then deep to the patellar ligament (proximal to the tibial tuberosity) using the substantially straight needle, and through the tibial tunnel using the substantially straight needle. The needles are cut off, and the sutures are tensioned over the repair site by using a tensioner, for example. Additional sutures may be provided to close the fascia and the skin.

BRIEF DESCRIPTION OF THE DRAWINGS

Other features and advantages of the present invention will become apparent when the following detailed description is read in conjunction with the accompanying drawings, in which.

DETAILED DESCRIPTION OF THE PREFERRED EMBODIMENT

The following description is provided to enable a person skilled in the art to make and use the invention and sets forth the best modes contemplated by the inventors of carrying out their invention. Various modifications, however, will remain readily apparent to those skilled in the art.

The present invention provides a method and apparatus for extracapsular ligament reconstruction in mammals, for example, CrCL reconstruction. The present invention employs a suture with a substantially curved (or substantially non-linear) needle at one end and a substantially straight (or substantially linear) needle at the other end. As described below, the suture is passed around the lateral fabella using the curved needle, then deep to the patellar ligament using the straight needle, and through the tibial tunnel using the straight needle.

Although the embodiments of the present invention will be described below with reference to an extracapsular canine ligament reconstruction (such as the CrCL reconstruction), the invention is not limited to this embodiment. Thus, the method of the present invention has applications to ligament reconstruction in general, and is not limited by the CrCL exemplary embodiment described below.

Figure 1:
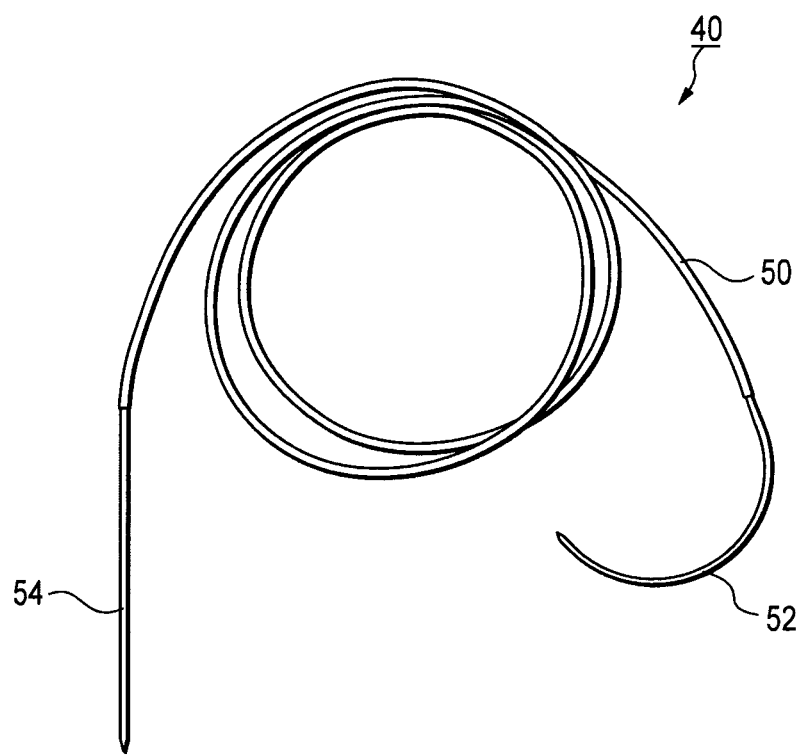
FIG. 1 illustrates the suture needle construct of the present invention, with a substantially curved needle attached to one end and a substantially straight or linear needle attached to the other end.

Referring now to the drawings, where like elements are designated by like reference numerals, FIG. 1 illustrates a suture needle construct 40 used for CrCL reconstruction. Suture needle construct 40 is formed of a length of suture 50 with a substantially curved needle 52 at one end and a substantially straight or linear needle 54 at the other end. Although FIG. 1 illustrates substantially curved needle 52 as a semicircle having a uniform radius, the invention is not limited to this exemplary embodiment, and contemplates curved needles having various non-linear configurations and geometries, such as an arcuate or bend configuration, or a bow configuration, or a combination of such configurations, among others. Thus, the semicircle configuration shown in FIG. 1 is only exemplary and the invention contemplates other substantially non-linear configurations for the curved needle 52.

In an exemplary embodiment, at least one of the two needles 52, 54 is a thin nitinol needle that allows an increased number of suture loop passes through, or around, the tissue to be attached or sutured with decreased trauma. Preferably, both needles 52, 54 are nitinol needles; however, other materials such as stainless steel, for example, may be employed for the needles. The needles may be swaged on the suture strand or on the plurality of suture strands. Alternatively, at least one of the needles may be free floating so that, after passing the suture loop construct through the tissue to be treated, one or both of the needles may be reoriented relative to each other.

Needles 52, 54 may be provided at each end of the suture (as shown in FIG. 1) or, alternatively, may be positioned on the length of the suture (i.e., not necessarily at the ends of the suture) and spaced apart from each other. In other embodiments, one needle may be positioned at one end of the suture whereas the other needle may be positioned anywhere on the length of the suture, as long as the needles are spaced apart from each other.

In a preferred embodiment, the suture attached to needles 52, 54 is formed of a high strength suture material such as Arthrex FiberWire suture, which is described in U.S. Pat. No. 6,716,234 to Grafton et al., the disclosure of which is incorporated by reference in its entirety. In additional embodiments, the suture may be a FiberWire suture of various colors to maximize repair strength, aid in suture management and provide superior tying characteristics. In an exemplary embodiment, the suture may be a #5 FiberWire, a particular high strength suture sold by Arthrex, Inc. of Naples, Fla. However, the invention is not limited to these exemplary embodiments and it must be understood that the invention contemplates various sizes and dimensions of the suture employed, depending on the size, age and breed of the animal ligament, among other factors. For example, in a canine CrCL repair, a #2 FiberWire is indicated for a smaller dog, while a #5 FiberWire is indicated for a larger dog such as Bernese mountain dog. Additionally, the invention also contemplates suture materials other than FiberWire, for example, monofilament sutures, Ethibond, or other braided sutures, among many others.

The suture attached to the needles 52, 54 may be employed as a single strand or as multiple strands, depending upon the size and characteristics of the ligament to be repaired. Thus, a two-strand suture between the two needles provides four strands of suture with one pass, increasing the strength characteristics. Although the invention is described with reference to a single strand of high strength suture 50 that is attached to needles 52, 54, the invention is not limited to this embodiment and encompasses embodiments where a plurality of continuous strands of suture 50, or continuous loops of suture 50, or a combination of continuous strands of suture 50 and continuous loops of suture 50, are attached to the two needles.

The method of ligament repair using the suture needle construct 40 of the present invention will be described below with reference to a particular exemplary embodiment. In this particular exemplary embodiment, the tissue to be treated is a canine CrCL that is repaired by passing the suture needle construct 40 of the present invention. Although the invention will be described with reference to this particular exemplary canine embodiment, it must be understood that the invention is not limited to this embodiment and contemplates ligament repairs in other mammals, such as cats, horses or cows. In addition, the invention also contemplates treatment (such as suturing or attachment, for example) of any ligament and tissue with the suture needle construct 40 described above. For example, the suture needle construct 40 may be employed to simply put stitches in a graft, in preparation for fixation with a fixation device such as an interference screw.

According to an exemplary embodiment, the tissue to be treated is a canine CrCL. FIGS. 2-9 illustrate the interior of a canine knee 90 in a lateral perspective undergoing the method of CrCL reconstruction using suture needle construct 40 of FIG. 1 according to the present invention. The joint is first explored and preparation of the knee cavity is conducted by removing any remaining articular cartilage using a combination of a rasp, curette and mechanical burr, for example. The patient is positioned in lateral or dorsal recumbency preferably under general anesthetic. A hanging limb technique with aseptic preparation and appropriate draping may be performed. A lateral parapatellar approach with arthrotomy may be performed and complete exploration of the stifle joint may be conducted. Pathologic ligament and meniscus should be treated appropriately. Once the joint is thoroughly lavaged, the joint capsule may be closed.

Figure 2:
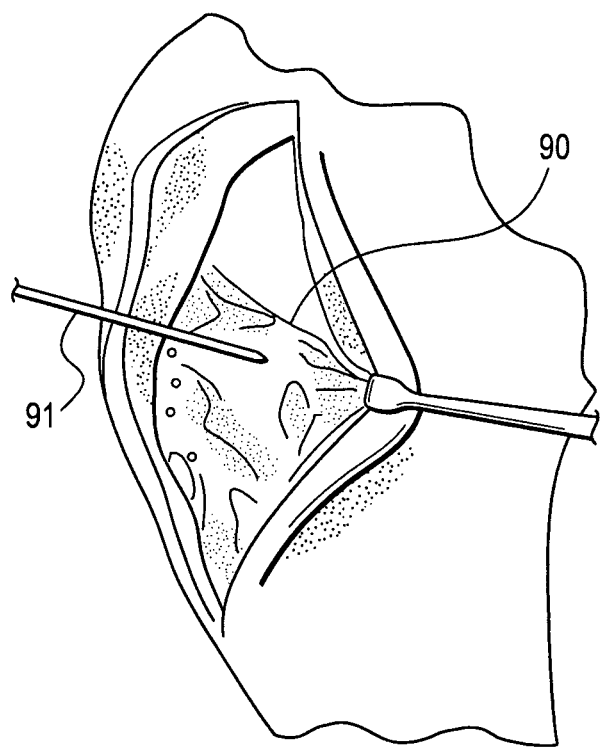
FIG. 2 is a lateral view of a canine knee undergoing a method of CrCL reconstruction according to the present invention.

Referring now to FIG. 2, after the joint capsule is closed, a combination of sharp and blunt dissection is used to separate the vastus lateralis and biceps femoris muscles and retract the biceps caudally, to allow for exposure and palpation of the lateral fabella (pin 91 pointing to it).

Figure 3:
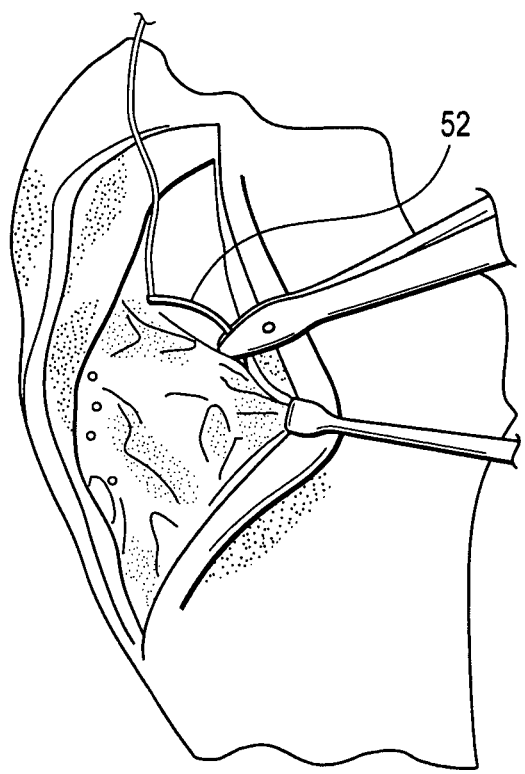
FIG. 3 illustrates the canine knee at a preparation stage subsequent to that shown in FIG. 2.

Suture needle construct 40 having a substantially curved needle 52 at one end of suture 50, and a substantially straight needle 54 at the other end of suture 50, is brought in the proximity of the joint. The substantially curved needle 52 is then placed with the tip on the midpoint of the lateral fabella and "walked" proximally until it can be inserted between the fabella and femur and passed completely around the fabella from proximal to distal. In this manner, the suture 50 is passed around the lateral fabella using the substantially curved needle 52, as shown in FIG. 3.

Figure 4:
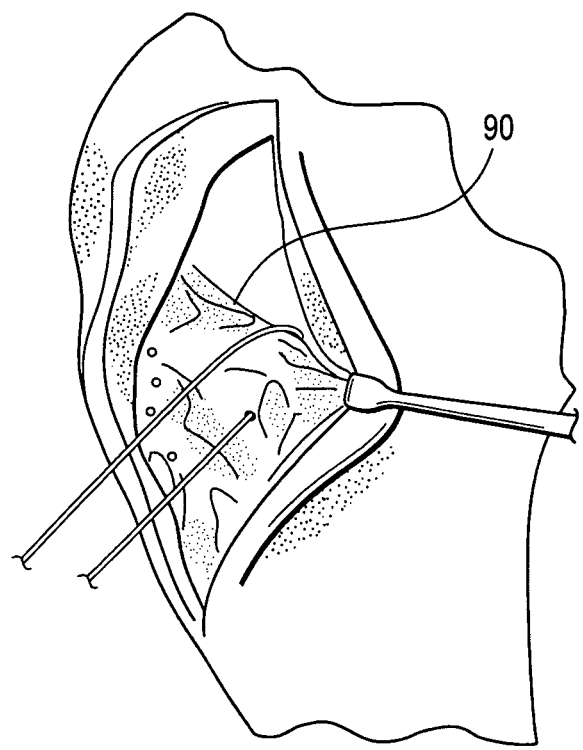
FIG. 4 illustrates the canine knee at a preparation stage subsequent to that shown in FIG. 3.

As shown in FIG. 4, the substantially curved needle 52 is preferably around the fabella and not caudal to it. This can be verified after suture placement by pulling on both strands of the suture 50 to ensure they are around the bone of the fabella and not soft tissues caudal to it. It is also important to minimize the amount of soft tissue encompassed in the suture throw, paying particular attention to the peroneal nerve distally. The substantially curved needle 52 is designed to help promote correct placement.

Figure 5:
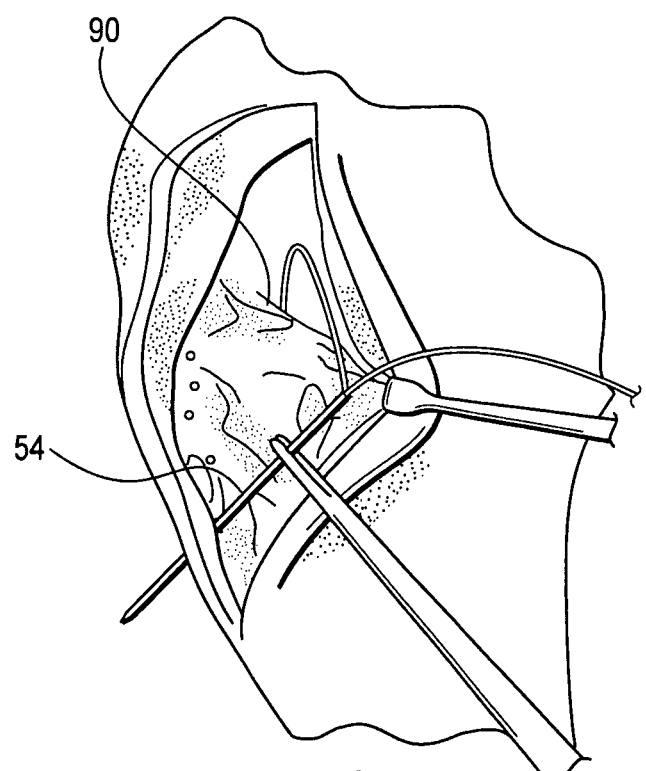
FIG. 5 illustrates the canine knee at a preparation stage subsequent to that shown in FIG. 4.

Reference is now made to FIG. 5. The substantially straight needle 54 at the opposite end of suture 50 is then passed deep to the patellar ligament from lateral to medial at the most distal point. At this point, the suture 50 should be caudal to the ligament and cranial to the fat pad.

Figure 6:
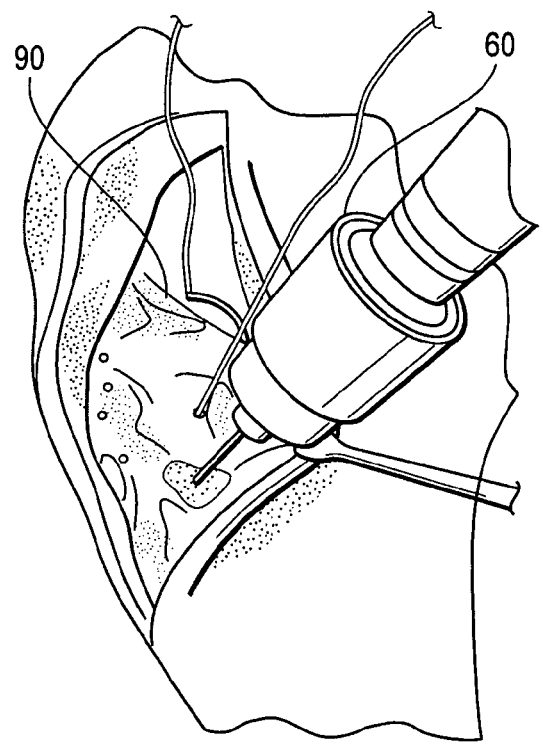
FIG. 6 illustrates the canine knee at a preparation stage subsequent to that shown in FIG. 5.
Figure 7:
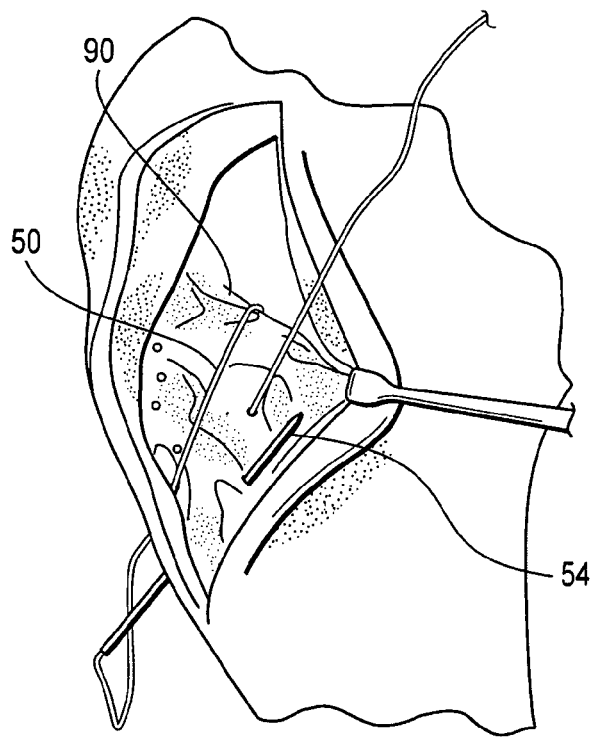
FIG. 7 illustrates the canine knee at a preparation stage subsequent to that shown in FIG. 6.

A hole (also referred to as "tunnel" or "socket") of about 2-3 mm is next created at the appropriate location in the proximal tibia for tibial fixation (FIG. 6). Preferably, the location of the tibial tunnel should be distal to Gerdy's tubercle and proximal to the point of origin of the cranial tibial muscle. The tibial tunnel should be slightly angled caudoproximal to craniodistal to match the final direction of the suture 50. The tibial tunnel may be formed by employing a drill 60 (FIG. 6), for example, to allow the substantially straight needle 54 to be inserted through the tibial tunnel, as shown in FIG. 7.

As the pin or drill is removed, the straight needle 54 of the suture needle construct 40 is inserted in the tibial tunnel from medial to lateral, and suture 50 is advanced to allow for easy tying.

Figure 8:
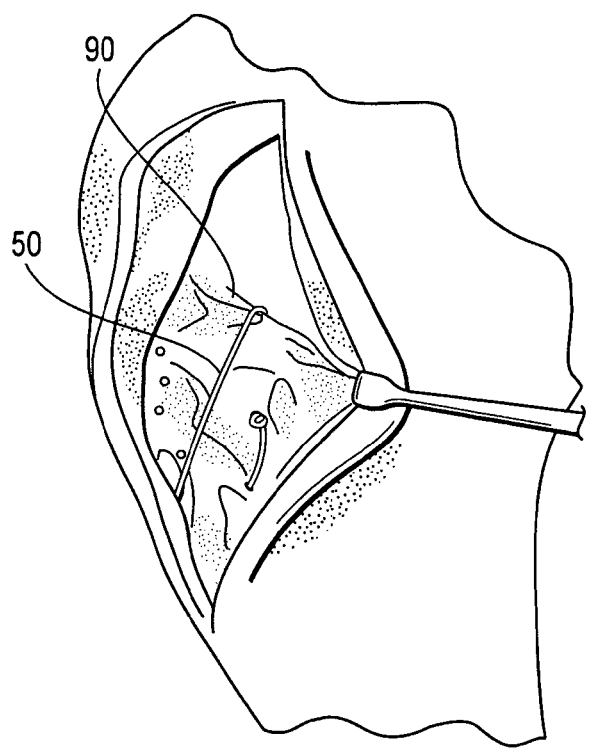
FIG. 8 illustrates the canine knee at a preparation stage subsequent to that shown in FIG. 7.

As shown in FIG. 8, both needles 52, 54 are cut off and the suture 50 is tied at the desired tension, to prevent abnormal cranial drawer and internal rotation. The stifle is then put through a range of motion to ensure the suture has been placed correctly and is not impinging on periarticular structures. The area may be lavaged. The ends of suture strand 50 are tied and tensioned over the repair site by using a tensioner, for example, to tension the suture knot to a specific poundage.

Figure 9:
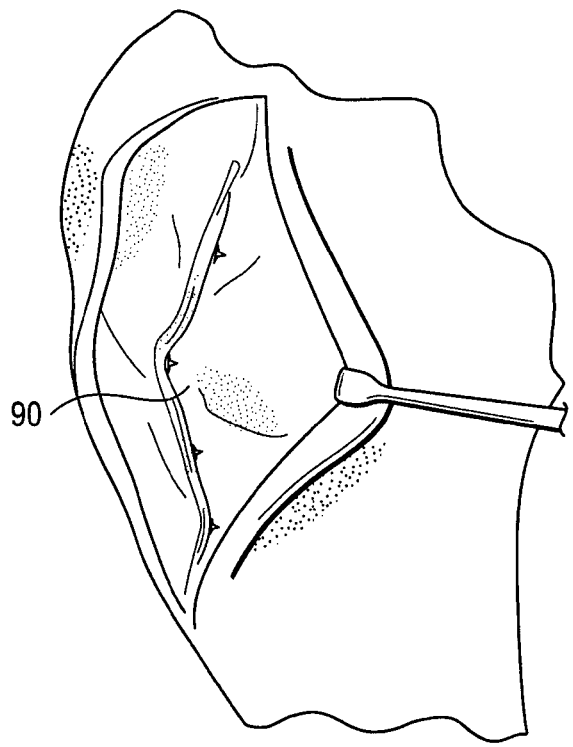
FIG. 9 illustrates the canine knee a preparation stage subsequent to that shown in FIG. 8.

Referring to FIG. 9, the lateral fascia is closed with the imbricating pattern of choice. Routine subcutaneous tissue and skin closures may be performed. Additional sutures may be provided to close the fascia and the skin.

Although the present invention has been described above with reference to an exemplary CrCL repair, the invention is not limited to this exemplary embodiment. Those skilled in the art will recognize that the structures and techniques disclosed can be used for ligament repair generally. Thus, the present invention contemplates tissue repairs, such as ligament repair, i.e., simple suturing of tissue, tendon to tendon repair, graft to bone repair, or tendon to bone repair, among others, with the suture needle construct 40 of the present invention.

In addition, although the present invention has been described in connection with preferred embodiments, many modifications and variations will become apparent to those skilled in the art. Thus, it is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. A method of extracapsular ligament repair, the method comprising the steps of:
   providing a bone tunnel into a bone of a mammal and adjacent a repair site of a capsular joint;
   providing a suture/needle construct in the proximity of the capsular joint, the suture/needle construct comprising a suture, a first needle provided at one end of the suture, and a second needle provided at the other end of the suture;
   passing the first needle around the capsule of the joint;
   subsequently passing the second needle in the vicinity of a ligament of the capsular joint; and
   passing the second needle through the bone tunnel.

2. The method of claim 1, wherein the first needle is a substantially curved needle and wherein the second needle is a substantially linear needle.

3. The method of claim 1, wherein the bone is tibia and the joint is a knee joint.

4. The method of claim 1, wherein the bone is a canine tibia and the joint is a canine knee joint.

5. The method of claim 1, wherein the ligament is the patellar ligament.

6. The method of claim 1, further comprising the step of cutting off at least one of the first and second needles and further tensioning remaining ends of the suture over the repair site.

7. The method of claim 1, wherein the suture comprises a single suture strand.

8. The method of claim 1, wherein the suture comprises a plurality of suture strands.

9. The method of claim 1, wherein the suture comprises a continuous loop of suture.

10. A method of canine CrCL repair, the method comprising the steps of:
    drilling a tibial tunnel adjacent a canine CrCL repair site of a knee joint;
    providing a suture/needle construct in the proximity of the repair site, the suture/needle construct comprising a suture, a substantially non-linear needle provided at one end of the suture, and a substantially linear needle provided at the other end of the suture;
    passing the substantially non-linear needle around the lateral fabella of the knee joint;
    subsequently passing the substantially linear needle under the patellar ligament of the knee joint;
    passing the substantially linear needle through the tibial tunnel;
    cutting off the substantially non-linear needle and the substantially linear needle to obtain at least two free ends of the suture; and
    tensioning the at least two free ends of the suture over the repair site.

11. The method of claim 10, further comprising the step of providing additional sutures to close fascia and skin at the repair site.

12. The method of claim 10, wherein the suture comprises at least one continuous loop of suture.

13. The method of claim 10, wherein the suture comprises a single suture strand.

14. The method of claim 10, wherein the suture comprises a high strength suture.

15. The method of claim 10, wherein the substantially non-linear needle has a configuration selected from the group consisting of semicircular, arcuate, bend, bowed and curved configuration.

* * * * *